(12) United States Patent
de Castro Guimarães Lopes Barbosa (10) Patent No.: US 12,378,063 B2
(45) Date of Patent: Aug. 5, 2025

(54) VEHICLE DELIVERY BOX SYSTEM AND METHOD

(71) Applicant: TUGA-GLOBAL, INC., Grand Haven, MI (US)

(72) Inventor: Cesar Manuel de Castro Guimarães Lopes Barbosa, Sintra (PT)

(73) Assignee: TUGA-GLOBAL, INC., Grand Haven, MI (US)

( * ) Notice: Subject to any disclaimer, the term of this patent is extended or adjusted under 35 U.S.C. 154(b) by 0 days.

(21) Appl. No.: 18/314,586

(22) Filed: May 9, 2023

(65) Prior Publication Data

US 2023/0356929 A1    Nov. 9, 2023

Related U.S. Application Data

(60) Provisional application No. 63/339,588, filed on May 9, 2022.

(51) Int. Cl.
*B65D 88/12* (2006.01)
*A61L 2/10* (2006.01)
(Continued)

(52) U.S. Cl.
CPC .............. *B65D 88/744* (2013.01); *A61L 2/10* (2013.01); *B60H 1/00985* (2013.01); *B60P 3/00* (2013.01); *B60R 25/01* (2013.01); *B65D 88/12* (2013.01); *B65D 88/14* (2013.01); *B65D 88/74* (2013.01); *B65D 90/48* (2013.01); *A61L 2202/23* (2013.01);
(Continued)

(58) Field of Classification Search
CPC ...... B65D 88/744; B65D 88/12; B65D 88/14; B65D 88/74; B65D 90/48; A61L 2/10; A61L 2202/23; B60H 1/00985; B60H 1/00264; B60H 3/00; B60P 3/00; B60R 25/01; B64U 2101/64; B64D 1/22
See application file for complete search history.

(56) References Cited

U.S. PATENT DOCUMENTS 10,440,863 B1 * 10/2019 Shelnutt .............. H05K 7/20745
2002/0130771 A1 * 9/2002 Osborne ............... B60C 23/008
340/441
(Continued)

FOREIGN PATENT DOCUMENTS

CN      104622516 A    5/2015
JP      2017505741 A   2/2017

OTHER PUBLICATIONS

Written Opinion of the International Searching Authority dated Nov. 22, 2023.

*Primary Examiner* — Toan C To
(74) *Attorney, Agent, or Firm* — Jacob M. Ward; Ward Law Office LLC (57) ABSTRACT

A vehicle delivery box for delivering content to a location using a transport vehicle is provided. The vehicle delivery box can include a main body having a first mode and a second mode. The main body can also include a cavity formed in the main body. The main body in the first mode can be removably coupled to the transport vehicle. The main body in the second mode can be uncoupled from the transport vehicle and adapted to deliver a product. Further, a vehicle delivery box system is provided including a vehicle delivery box and a transport vehicle. A method for delivering a product is also provided.

18 Claims, 4 Drawing Sheets

(51) Int. Cl.

|  |  |
|---|---|
| *B60H 1/00* | (2006.01) |
| *B60P 3/00* | (2006.01) |
| *B60R 25/01* | (2013.01) |
| *B65D 88/14* | (2006.01) |
| *B65D 88/74* | (2006.01) |
| *B65D 90/48* | (2006.01) |
| *B60H 3/00* | (2006.01) |
| *B64D 1/22* | (2006.01) |
| *B64U 101/64* | (2023.01) |

(52) U.S. Cl.
CPC ............ *B60H 1/00264* (2013.01); *B60H 3/00* (2013.01); *B64D 1/22* (2013.01); *B64U 2101/64* (2023.01)

(56) References Cited

U.S. PATENT DOCUMENTS

| | | |
|---|---|---|
| 2007/0069877 A1* | 3/2007 | Fogelstrom ............ B60C 23/005 340/442 |
| 2008/0042817 A1* | 2/2008 | Fogelstrom ............ B60C 23/009 340/442 |
| 2017/0267348 A1 | 9/2017 | Sweeny et al. |
| 2019/0034857 A1* | 1/2019 | Ferguson .............. G05D 1/0038 |
| 2019/0314535 A1 | 10/2019 | Golkowski et al. |
| 2021/0229770 A1 | 7/2021 | Schultz et al. |
| 2022/0108377 A1 | 4/2022 | Ferguson et al. |
| 2024/0127164 A1* | 4/2024 | Shayne ............... G06Q 10/0833 |

\* cited by examiner

VEHICLE DELIVERY BOX SYSTEM AND METHOD

CROSS-REFERENCE TO RELATED APPLICATIONS

This application claims the benefit of U.S. Provisional Application No. 63/339,588, filed on May 9, 2022. The entire disclosure of the above application is incorporated herein by reference.

FIELD

The present technology relates to a delivery method and, more particularly, a vehicle delivery box for delivering a product.

INTRODUCTION

This section provides background information related to the present disclosure which is not necessarily prior art.

The need for local delivery services has steadily risen since the 1960s, when pizzerias first began delivering pizza to consumers' homes. Since then, local delivery service has expanded to deliver not just pizza, but all types of products, such as takeout, groceries, and prescriptions. To aid with the rising demand for quick delivery service, services such as Door Dash, Grub Hub, Post Mates, and Uber Eats have been developed. These services allow any person to instantly become a delivery driver.

The majority of delivery drivers use an automotive vehicle to make their deliveries. Using an automotive vehicle requires the delivery driver to physically get into the vehicle, drive it to the pickup location, gather the product being delivered from the pickup location, and transport the product to its destination. This way of delivering products takes significant time, especially if a driver is delivering one product at a time to keep the product as fresh as possible. Further, some deliveries can be very heavy. If a family's entire grocery order for a week is being delivered, the driver may need to make several trips back and forth to the car in order to deliver all of the groceries. Carrying the delivery up several flights of stairs in an apartment building or even down a long path adds even more time to the delivery.

In order to save time, some delivery drivers will deliver multiple products at once. Although this may save the delivery driver time, the consumer receiving the product typically must wait longer because the driver may deliver one or more other products first. Additionally, taking more than one order to save time may result in products not delivered first deteriorating in quality; e.g., a freshly baked pizza may cool below the desired temperature. Standard automotive vehicles do not have the ability to keep the product being delivered at optimal environmental conditions. Food may get shuffled around, cool off, or even melt during transport in a standard vehicle, and the longer a product is driven around, the more likely the product may deteriorate with respect to one of these conditions.

There is a continuing need for a vehicle delivery box that can aid with the delivery process and maintain optimum environmental conditions for one or more products. Desirably, a delivery box that may be easily removed from a vehicle and that may be wheeled or transported by drone is needed. Accordingly, there is a continuing need for an improved vehicle delivery box.

SUMMARY

In concordance with the instant disclosure, a vehicle delivery box that can aid with the delivery process and maintain optimum environmental conditions for one or more products, has surprisingly been discovered.

In one embodiment, a vehicle delivery box for delivering content to a location using a transport vehicle is provided. The vehicle delivery box can include a main body having a first mode and a second mode. The main body can also include a cavity formed in the main body. The main body in the first mode can be removably coupled to the transport vehicle. The main body in the second mode can be uncoupled from the transport vehicle and adapted to deliver a product.

In another embodiment, a vehicle delivery box system is provided. The vehicle delivery box system can include a vehicle delivery box and a transport vehicle. The vehicle delivery box can include a main body having a first mode and a second mode. The main body can also include a cavity formed in the main body. The main body in the first mode can be removably coupled to the transport vehicle. The main body in the second mode can be uncoupled from the transport vehicle and adapted to deliver a product.

In a further embodiment, a method for delivering a product is provided. A vehicle delivery box and transport vehicle can be provided. The vehicle delivery box can include a main body having a first mode and a second mode. The main body can also include a cavity formed in the main body. The main body in the first mode can be removably coupled to the transport vehicle. The main body in the second mode can be uncoupled from the transport vehicle and adapted to deliver a product. The vehicle delivery box can be disconnected from the vehicle delivery box to place the vehicle delivery box in the second mode. The vehicle delivery box can be operated to deliver the product to the location spaced apart from the transport vehicle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9,1-8,1-3,1-2,2-10,2-8,2-3,3-10,3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology relates to a vehicle delivery box 100, a vehicle delivery box system 200, and a method 300 for delivering a product to a location with a vehicle delivery box 100, shown generally in FIGS. 1-6. Advantageously, the vehicle delivery box 100 can provide an efficient and time saving means for transporting one or more various products, where different products may require specific transporting conditions.

Figure 1A:
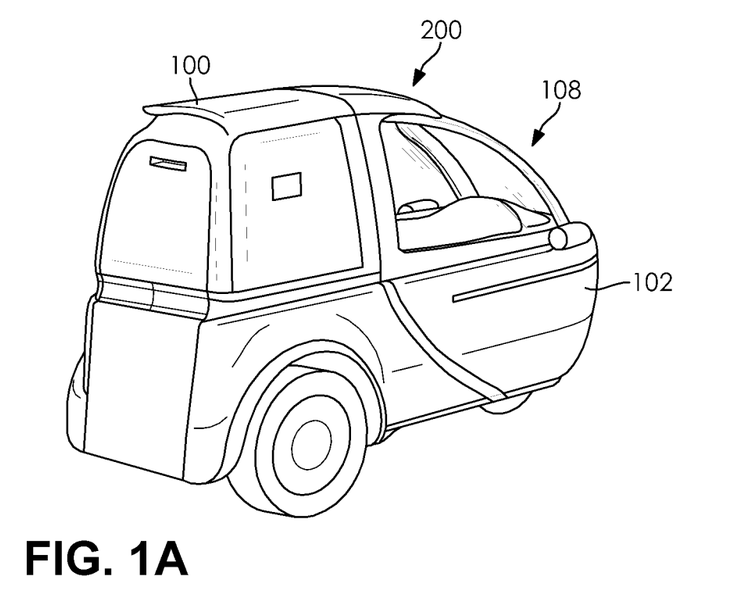
FIG. 1A is a top perspective view of a vehicle delivery system including a vehicle delivery box in a first mode coupled to a transport vehicle.
Figure 1B:
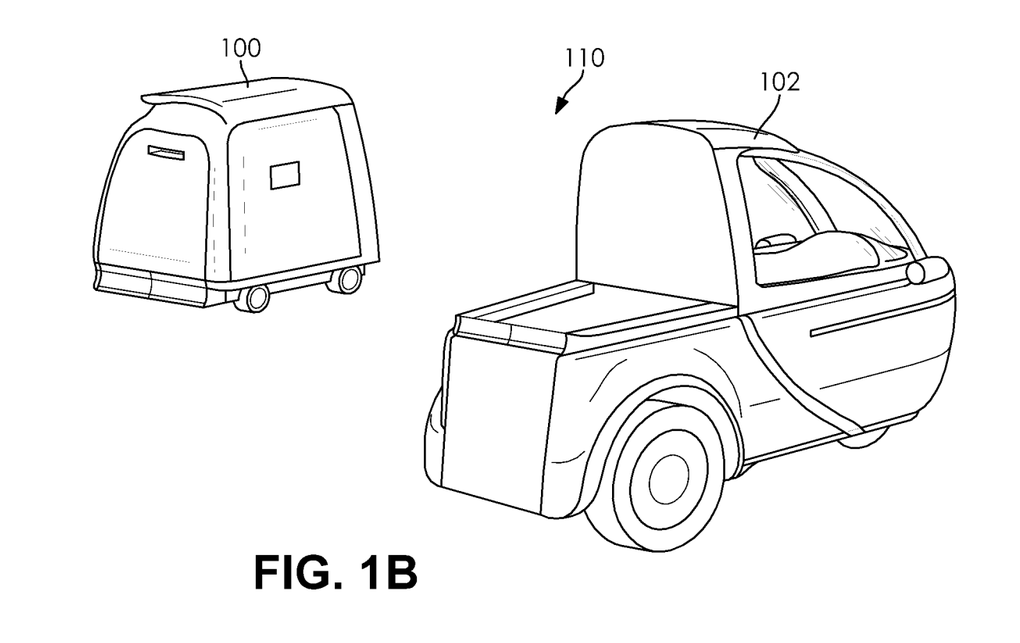
FIG. 1B is a top perspective view of the vehicle delivery system including the vehicle delivery box in a second mode decoupled from the transport vehicle.

As shown in FIGS. 1-4, the vehicle delivery box 100 for delivering a product to a location using a transport vehicle 102. The vehicle delivery box 100 can include a main body 104 having a cavity 106. The main body 104 can have a first mode 108 and a second mode 110, as shown in FIG. 1. Where the main body 104 is in the first mode 108, shown in FIG. 1A, the main body 104 can be removably coupled to the transport vehicle 102. Where the main body 104 is in the second mode 110, shown in FIG. 1B, the main body 104 can be uncoupled from the transport vehicle 102 and adapted to deliver a product.

Figure 2:
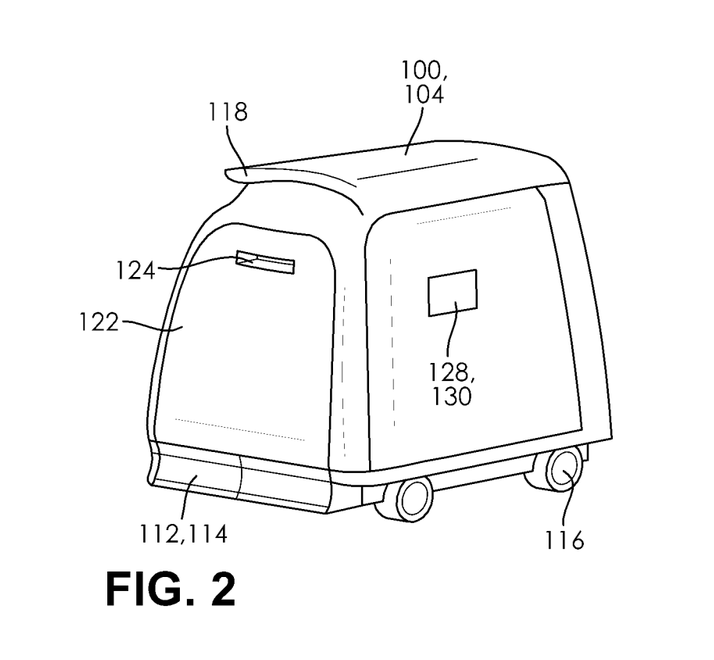
FIG. 2 is a top perspective view of the vehicle delivery box.

As shown in FIG. 2, the main body 104 can include a mating means 112. The mating means 112 can be configured to connect the main body 104 to the transport vehicle 102 in the first mode 108, shown in FIG. 1A. As a non-limiting example, the mating means 112 can include a recess 114 formed on an outer surface of the main body 104. The recess 114 can be configured to slidably connect with a rail disposed on the transport vehicle 102. As a further example, the mating means 112 can be clamps disposed on an outer surface of the main body 104 and configured to snap to a protrusion disposed on the transport vehicle 102. Advantageously, the mating means 112 can allow for the vehicle delivery box 100 to be quickly and easily removed from the transport vehicle 102. A skilled artisan can select a suitable mating means 112 within the scope of the present disclosure.

Figure 3:
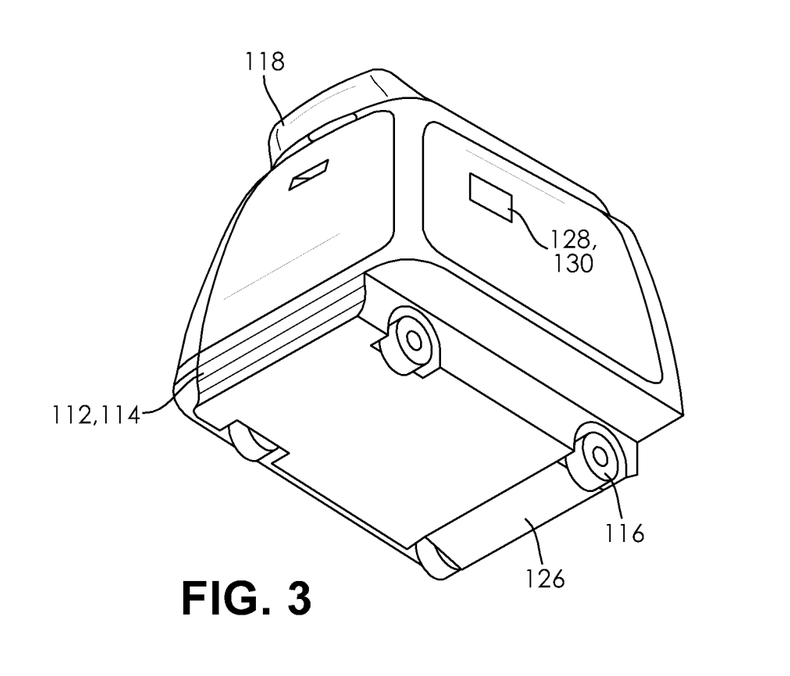
FIG. 3 is a bottom perspective view thereof.

In should be appreciated that the vehicle delivery box 100 can include a wheel 116 depending from the main body 104. In an exemplary embodiment, the vehicle delivery box 100 can include four wheels, as shown in FIG. 3. The wheels 116 can allow for the vehicle delivery box 100 to move to a location spaced apart from the transport vehicle 102 when the vehicle delivery box 100 is in the second mode 110. Advantageously, the wheels 116 permit the vehicle delivery box 100 to be moved without being lifted by a user. The wheels 116 allow for the vehicle delivery box 100 to be rolled, pushed, pulled, or, in certain circumstances, to be moved by a robot and/or drone via a controller or autonomously, described hereinbelow. A skilled artisan can select a suitable number of wheels 116 to facilitate the movement of the vehicle delivery box 100.

As shown in FIG. 2, the main body 104 can include a handle 118. The handle 118 can be configured to allow for the user to carry the vehicle delivery box 100 where it is in the second mode 110 uncoupled to the transport vehicle 102. As a non-limiting example and as shown in FIG. 2, the handle 118 can be configured to extend from an exterior of the main body 104 to allow for the vehicle delivery box 100 to be pulled while in the second mode 110, should the user wish to manually move vehicle delivery box 100. Alternatively, the main body 104 can include two handles to allow for the vehicle delivery box 100 to be carried while in the second mode 110 from the transport vehicle 102 to the location spaced apart from the transport vehicle 102. A skilled artisan can select a suitable number of handles 118 for moving the vehicle delivery box 100, as desired.

Figure 4:
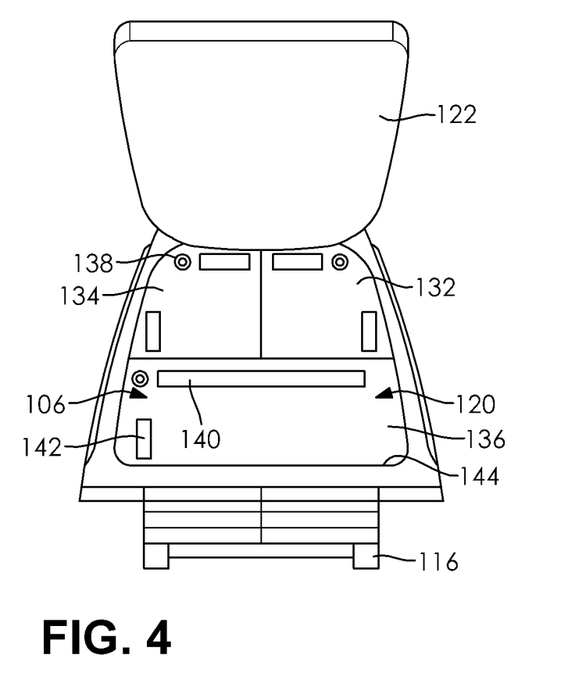
FIG. 4 is a front elevational view of a cavity of the vehicle delivery box.

With reference to FIG. 4, the main body 104 can include an opening 120 configured to allow the user to access the cavity 106 within the main body 104, and therefore, load or remove one or more products within the main body 104. The opening 120 can be of a variable size dependent upon the dimensions of the product and the number of products required to be transported. A skilled artisan can select suitable dimensions for the opening 120, as desired. The main body can also include a door 122 configured to fit the opening 120 and close off the cavity 106 of the main body 104 from outside conditions and exposure. The door 122 can create a fluid tight and airtight seal with the main body 104. Advantageously, the fluid tight seal can keep the product safe during travel. As a non-limiting example, the door 122 can be one of a hinged door, a sliding door, and a folding door, and a skilled artisan can select a suitable type of door 122, as desired. The door 122 can open to one side or, alternatively, can open upward, as shown in FIG. 4.

With renewed reference to FIG. 2, the door 122 can include a locking system 124. As described hereinabove, the door 122 can be configured to close off the cavity 106 and keep the product within the vehicle delivery box 100 safe from conditions outside the vehicle delivery box 100. Further, the locking system 124 can protect the product within the vehicle delivery box 100 from being removed by someone other than the user by requiring a passcode, a key, or personal identification, as examples, to gain access to the cavity 106 through the door 122.

As shown in FIG. 3, the main body 104 can include a battery 126 configured to provide power to the vehicle delivery box 100 such that it can maintain specific conditions within the main body 104 when the main body 104 is in the second mode 110, uncoupled from the transport vehicle 102. Advantageously, the battery 126 can maintain the temperature and humidity of the cavity 106, as well as preserve a sterile environment within the cavity, as the product may require. Further, the battery 126 permits the user to use any electrical component of the vehicle delivery box, such as lights, a user interface and display, or motorized movement via controller, while in the first mode 108 or the second mode 110. The battery 126 can also power the vehicle delivery box 100 for transport while in the second mode. To this point, while in operation, the user can use a controller to direct the vehicle delivery box 100 while it is powered by the battery 126. A skilled artisan can select other such features for the battery 126 to power, as desired.

It should be appreciated that in certain embodiments, where the main body 104 is in the first mode 108 coupled to the transport vehicle 102, the transport vehicle 102 can supply the power needed to maintain specific conditions within the main body 104. Alternatively, the battery 126 can be configured to power the main body 104 in the first mode 108. The user can select a power source for the main body 104 in the first mode 108 and can alternate between battery 126 and the transport vehicle 102 while the vehicle delivery box 100 and transport vehicle 102 are in use. For example, should the battery 126 die while the main body 104 is coupled to the transport vehicle 102, the transport vehicle 102 can automatically resume powering the main body 104 to maintain conditions within the main body 104. Additionally, the transport vehicle can be configured to recharge the battery of the main body 104 while in the first mode 108 to allow for the battery to maintain conditions within the main body 104 while in the second mode 110 spaced away from the transport vehicle 102.

As shown in FIGS. 2-3, the main body 104 can include a display unit 128. The display unit 128 can be configured to relay the conditions within the vehicle delivery box 100, or alternatively, within different compartments of the vehicle delivery box 100, to the user. The conditions that can be communicated to the user can include temperature, humidity, and sterileness, as examples. The display unit 128 can be disposed on the exterior of the main body 104 to be viewed by the user. In some embodiments, the display unit 128 can include a user interface 130 configured to modify the conditions within the cavity 106. The user interface 130 provides the user with a means of modifying the conditions within the cavity directly on the main body 104 and militates against the user having the user another system, such as a mobile device or user interface within the transport vehicle, to modify the conditions or having to enter the cavity 106 itself to adjust the conditions. In an alternative embodiment, the conditions within the cavity 106 can be controlled by a separate device. For example, the separate device can be a mobile device, an application for a mobile device, a controller, or a control unit within the transport vehicle, which can allow for the conditions within the main body 104 to be altered without the user being near the main body 104. A skilled artisan can select a suitable means for modifying the conditions within the vehicle delivery box 100, as desired.

With renewed reference to FIG. 4, the cavity 106 can include compartments 132 and, in some embodiments, the cavity 106 can be divided into a variable number of compartments. Each of the compartments 132 can be configured to maintain different conditions. As non-limiting example, each of the compartments 132 can maintain a different temperature with a first compartment 134 maintaining a first temperature and a second compartment 136 maintaining a second temperature. Other such examples of configurable conditions include, but are not limited to, humidity and sterileness. A skilled artisan can select suitable customizable conditions to be varied within each of the compartments 132.

With continued reference to FIG. 4, the cavity 106 can include a sensor 138. The sensor 138 can be configured to monitor at least one of the conditions within the vehicle delivery box 100 such as temperature, weight, and humidity. The sensor 138 can be in communication with the display unit 128 to relay the conditions within the vehicle delivery box 100 to the user. This enables the user to make modifications to the conditions within the vehicle delivery box 100 while the vehicle delivery box 100 is in the first mode 108 attached to the transport vehicle 102. Alternatively, the user can modify the conditions and receive feedback to the change in condition monitored by the sensor 138 while the vehicle delivery box 100 is in the second mode 110 at a location spaced away from the transport vehicle 102. Desirably, this alternative enables the user to modify the conditions while the vehicle delivery box 100 is not with the user.

It should be noted that in another embodiment, each of the compartments 132 can include a sensor 138 configured to monitor at least one of the conditions within the vehicle delivery box 100 such as temperature, weight, and humidity. Advantageously, this can permit each of the compartments 132 to have individualized conditions to meet the specific needs of the product(s) within the compartments 132. For example, the temperature and humidity within a first compartment 134 containing food can differ from the temperature and humidity within a second compartment 136 containing medication. The sensor 138 can relay to the display unit 128 the conditions within each compartment 132 and allow for the user to modify the conditions within each compartment 132, whether the vehicle delivery box 100 is in the first mode 108 or the second mode 110.

As shown in FIG. 4, each one of the compartments 132 can include an internal sanitation system 140. The sanitation system 140 be configured to destroy bacteria within each of the compartments 132. As a non-limiting example, the sanitation system 140 can include a UV light system. The sanitation system 140 can be in communication with the display unit 128 to relay the sterileness within the vehicle delivery box 100 to the user. In one embodiment, the sanitation system 140 can be disposed in the cavity 106 to sanitize the entirety of the cavity 106. Alternatively, the sanitation system 140 can be disposed within each of the compartments 132 or a portion of the compartments 132 to allow each compartment 132 to maintain different sanitation standards.

As shown in FIG. 4, each one of the compartments 132 can include a temperature control system 142 configured to regulate the temperature within the compartment 132. The temperature control system 142 can be in communication with the display unit 128 to relay the temperature within the vehicle delivery box 100 to the user. In one embodiment, the temperature control system 142 can be disposed in the cavity to control the temperature of the entirety of the cavity 106. Alternatively, the temperature control system 142 can be disposed within each of the compartments 132 or a portion of the compartments 132 to allow each compartment 132 to maintain different temperature requirements. As an example, the temperature control system 142 can maintain the temperature in the first compartment 134 to maintain the temperature to keep food or medicine warm, while temperature in the second compartment 136 can be maintained at a temperature to keep food or medicine frozen.

It should be appreciated that the ability to modify and customize the conditions within one compartment 132 independently of the conditions maintained in another compartment 132 allows for the products transported by the vehicle delivery box 100 to be highly varied. Products of varied types, temperatures, and humidity can be transported in a singular trip without the user worrying that the products could be spoiled or ruined. The ability to reduce the number of trips required to deliver varying products can maximize delivery efficiency and therefore reduce delivery time and fuel costs.

As shown in FIG. 4, the cavity 106 can include an auto balance floor 144. The auto balance floor 144 can allow the product being transported to remain level while in the vehicle delivery box 100. The auto balance floor 144 can maintain the positioning of any number of compartments 132 within the main body 104 by sustaining the entirety of the cavity 106 in a state of balance. Desirably, in a non-limiting example, if the vehicle delivery box 100 is delivering food, the food can remain upright to militate against slipping or shuffling.

Figure 5:
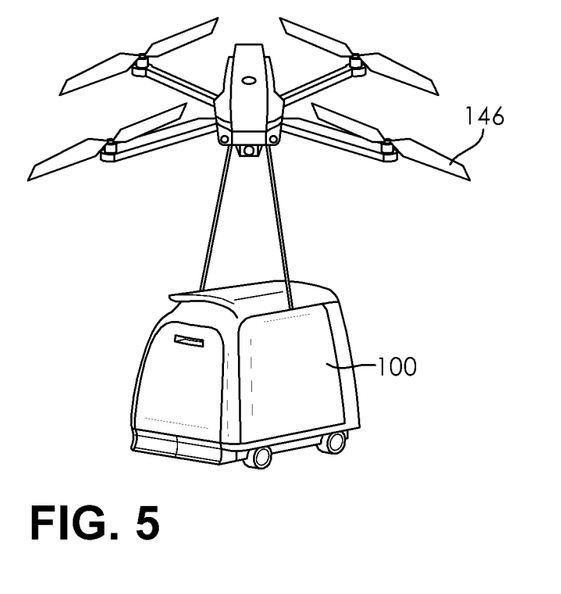
FIG. 5 is an environmental view of a vehicle delivery box being transported via an unmanned aircraft system.

As shown in FIG. 5, the vehicle delivery box 100 can be configured to depend from an unmanned aircraft system 146. As non-limiting examples, the unmanned aircraft system 146 can be a quadcopter, hexacopter, or octocopter. A skilled artisan can select a suitable unmanned aircraft system 146. Desirably, the unmanned aircraft system 146 can allow the product(s) within the vehicle delivery box 100 to be delivered autonomously. For example, the transport vehicle driver could use the unmanned aircraft system 146 while approaching the location where the respective product is to be delivered. In operation, the transport vehicle driver or user, if the transport vehicle is autonomous as described hereinabove, could remain in the transport vehicle 102 and control the vehicle delivery box 100 using the unmanned aircraft system 146 to transport the vehicle delivery box 100 to the final location that is spaced apart from the transport vehicle 102. A skilled artisan can select the maximum distance the unmanned aircraft system 146 can transport the vehicle delivery box 100.

The present disclosure also contemplates a vehicle delivery box system 200. The vehicle delivery box system 200 can include a vehicle delivery box 100, as described hereinabove, and a transport vehicle 102. It should be appreciated that, as an example, the transport vehicle 102 can be a vehicle such as described by U.S. patent application Ser. No. 17/159,507 NARROW THREE WHEELED VEHICLE WITH STABILIZING AND MODULAR MECHANISMS filed on Jan. 27, 2021, incorporated herein by reference. A skilled artisan can select a suitable transport vehicle 102 that is compatible with the vehicle delivery box 100.

As shown in FIG. 5, the transport vehicle 102 can be an unmanned aircraft system 146. As non-limiting examples, the unmanned aircraft system 146 can be a quadcopter, hexacopter, or octocopter. A skilled artisan can select a suitable unmanned aircraft system 146. Desirably, the unmanned aircraft system 146 can allow the product within of the vehicle delivery box 100 to be delivered autonomously. In operation, the unmanned aircraft system 146 can be connected to the vehicle delivery box 100 for the product to be transported via a controller or preprogrammed route to the delivery location. Upon arrival at the delivery location, the unmanned aircraft system 146 can be in the second mode and therefore uncoupled from the vehicle delivery box 100. A skilled artisan can select the maximum distance the unmanned aircraft system 146 can transport the vehicle delivery box 100.

Figure 6:
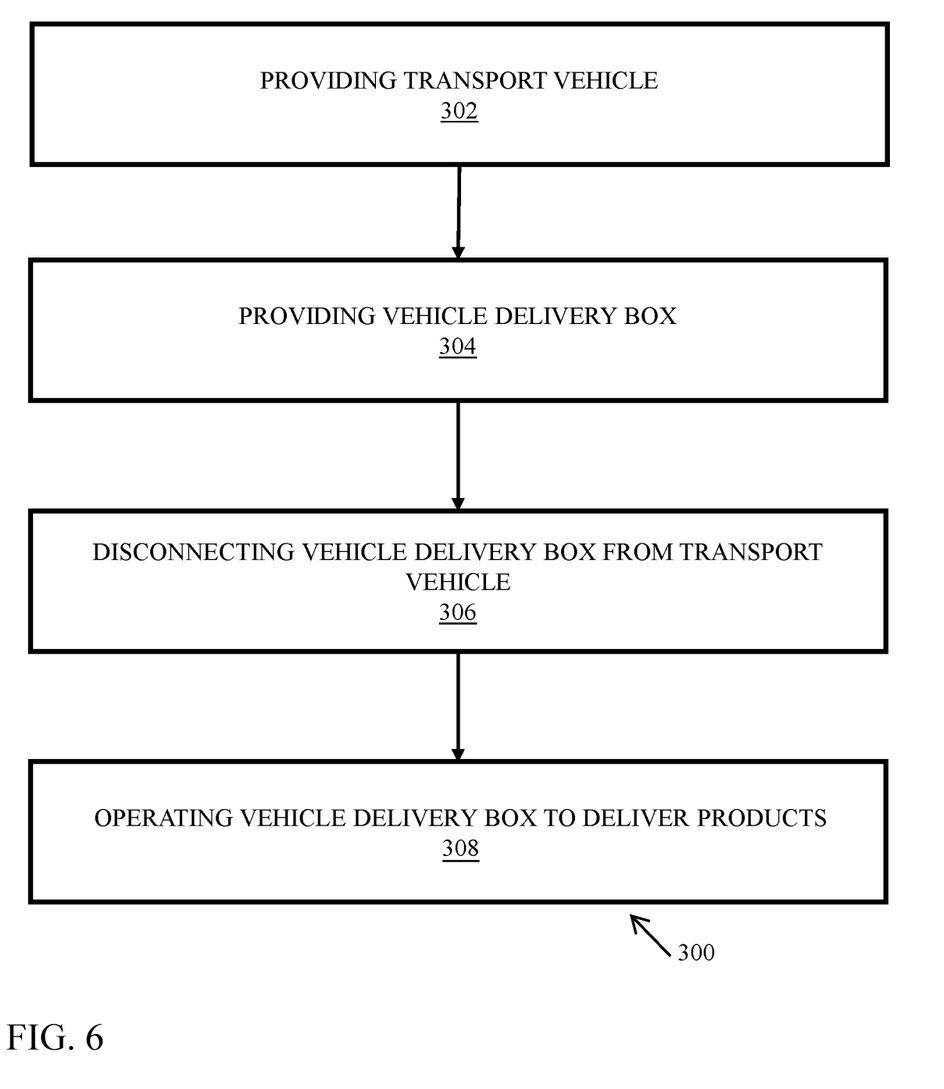
FIG. 6 is a flow diagram of a method for delivering a product with a vehicle delivery box.

The present disclosure further provides the method 300 for delivering a product with a vehicle delivery box 100 shown in FIG. 6. In a step 302, a transport vehicle 102 can be provided. As described hereinabove, the transport vehicle 102 can be a three-wheeled vehicle. In another embodiment, the transport vehicle can be an unmanned aircraft system and can further be autonomous. A vehicle delivery box 100, as described hereinabove, can be provided in a step 304. The vehicle delivery box 100 can be in the first mode 108 coupled to the transport vehicle 102. In a step 306, the vehicle delivery box 100 can be disconnected from the transport vehicle 102, thereby moving from the first mode 108 to the second mode 110. The vehicle delivery box 100 can be operated to deliver the product contained within the vehicle delivery box 100 to a location spaced apart from the vehicle in a step 308. More specifically, the vehicle delivery box 100 can be operated via a controller or can operate autonomously.

Advantageously, the vehicle delivery box 100 of the present disclosure provides the ability to modify and customize the conditions within one compartment independently of the conditions maintained in another compartment, which allows for the products transported by the vehicle delivery box 100 to be highly varied. Products requiring different conditions, such as temperature and humidity, can be transported in a singular trip without the user worrying that the products could be spoiled or ruined. The ability to reduce the number of trips required to deliver varying products can maximize delivery efficiency and therefore reduce delivery time and fuel costs.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A vehicle delivery box for delivering a product to a location using a transport vehicle, comprising:
a main body having a first mode and a second mode; and
a cavity formed in the main body, the cavity including a plurality of compartments,
wherein the main body in the first mode is removably coupled to the transport vehicle and the main body in the second mode is uncoupled from the transport vehicle and adapted to deliver the product,
wherein one of the compartments includes a sanitation system configured to destroy bacteria.

2. The vehicle delivery box of claim 1, wherein the main body includes a mating means configured to removably connect the main body to the transport vehicle in the first mode.

3. The vehicle delivery box of claim 2, wherein the mating means includes a recess formed on an outer surface of the main body configured to slidably connect with the transport vehicle.

4. The vehicle delivery box of claim 1, wherein a wheel depends from the main body.

5. The vehicle delivery box of claim 1, wherein the cavity includes a sensor.

6. The vehicle delivery box of claim 5, wherein the sensor is configured to monitor at least one of temperature, weight, and humidity.

7. The vehicle delivery box of claim 1, wherein the cavity includes an auto balance floor.

8. The vehicle delivery box of claim 1, wherein the main body includes a door having a locking system.

9. The vehicle delivery box of claim 8, wherein the locking system is configured to create an airtight seal.

10. The vehicle delivery box of claim 1, wherein the main body includes a display unit configured to display conditions within the vehicle delivery box.

11. The vehicle delivery box of claim 10, wherein the display unit includes a user interface configured to modify at least one of at least one of temperature, sterileness, and humidity within the main body.

12. The vehicle delivery box of claim 1, wherein the main body includes a battery configured to power the vehicle delivery box independently of the transport vehicle.

13. The vehicle delivery box of claim 1, wherein one of the compartments includes a temperature control system configured to regulate a temperature of the one of the compartments.

14. The vehicle delivery box of claim 1, wherein the main body includes a handle.

15. A vehicle delivery box system for delivering a product to a location, comprising:
a transport vehicle; and
a vehicle delivery box including:
a main body having a first mode and a second mode, and
a cavity formed in the main body, the cavity including a plurality of compartments,
wherein the main body in the first mode is removably coupled to the transport vehicle and the main body in the second mode is uncoupled from the transport vehicle and adapted to deliver the product,
wherein one of the compartments includes a sanitation system configured to destroy bacteria.

16. The vehicle delivery box system of claim 15, wherein the transport vehicle is autonomous.

17. The vehicle delivery box system of claim 15, wherein the transport vehicle includes an unmanned aircraft system.

18. A vehicle delivery box for delivering a product to a location using a transport vehicle, comprising:
a main body having a first mode and a second mode, the main body including:
a mating means configured to removably connect the main body to the transport vehicle in the first mode,
a door including a locking system configured to create an airtight seal, a display unit configured to display conditions within the main body and modify at least one of temperature, sterileness and humidity within the main body, a battery configured to power the main body; and a cavity formed in the main body including:

a plurality of compartments, one of the compartments including at least one of a sanitation system configured to destroy bacteria and a temperature control system configured to regulate a temperature within the compartment, a sensor, an auto balance floor, the sensor configured to monitor at least one of temperature, weight, and humidity, wherein the main body in the first mode is removably coupled to the transport vehicle and the main body in the second mode is uncoupled from the transport vehicle and adapted to deliver the product.

\* \* \* \* \*